US005458853A

United States Patent [19]
Porter et al.

[11] Patent Number: 5,458,853
[45] Date of Patent: Oct. 17, 1995

[54] BREATH ANALYSIS DEVICE

[75] Inventors: Anthony Porter, Middle Dural; Robert Breakspere, Yowie Bay, both of Australia

[73] Assignee: Lion Analytics Pty. Ltd., Castle Hill, Australia

[21] Appl. No.: 129,806

[22] Filed: Sep. 30, 1993

Related U.S. Application Data

[63] Continuation of Ser. No. 895,567, Jun. 5, 1992, abandoned, which is a continuation of Ser. No. 503,814, Apr. 3, 1990, abandoned.

[30] Foreign Application Priority Data

Apr. 3, 1989 [AU] Australia ................................. PJ3492

[51] Int. Cl.$^6$ ................................................. G01N 1/22
[52] U.S. Cl. .............................. 422/84; 73/23.3; 128/719; 436/132; 436/900
[58] Field of Search .............................. 422/84; 436/132, 436/148, 900; 128/719; 73/23.3

[56] References Cited

U.S. PATENT DOCUMENTS

| | | | |
|---|---|---|---|
| 4,749,553 | 6/1988 | Lopez et al. | 436/132 |
| 4,902,628 | 2/1990 | Blair | 422/84 |
| 4,996,161 | 2/1991 | Conners et al. | 422/84 |

FOREIGN PATENT DOCUMENTS

| | | |
|---|---|---|
| 8707723 | 12/1987 | WIPO . |
| 8707724 | 12/1987 | WIPO . |

*Primary Examiner*—W. Gary Jones
*Assistant Examiner*—Laura E. Edwards
*Attorney, Agent, or Firm*—Ladas & Parry

[57] ABSTRACT

A dual breath analysis device having a passive first mode of testing and analysing an exhaled breath sample without the use of a mouthpiece, and a second mode of testing and analysing a second breath sample through a mouthpiece apparatus when the first mode of testing indicates a substantially high level of alcohol in the first breath sample.

4 Claims, 4 Drawing Sheets

| NON INVASIVE MESSAGES | * DIRECT MESSAGES | * OTHER FEATURES |
|---|---|---|
| LION ANALYSTICS DUAL SCREENER | 10:08:40 WED 20TH SEPT 89 | PLEASE WAIT |
| CHANGE BATTERIES | NUMBER OF TESTS IN BATTS=79 | SERVICE REQUIRED |
| PASSIVE TEST PRESS TO SAMPLE | DIRECT TEST: SET MOUTHPIECE | BACKLIGHT OFF |
| SAMPLING INJECT :1 | VOLUME = 1300ml | BACKLIGHT ON |
| SAMPLING INJECT :2 | VOLUME = 0ml RETEST | PRESS ONCE TO POWER OFF |
| SAMPLING INJECT :3 | MANUAL INJECT: PRESS TO SAMPLE | PRESS ONCE TO START PRINT |
| ANALYSING SAMPLE PLEASE WAIT | MANUAL INJECT: | PRINTING |
| PASS | VOLUME = 1300ml STOP BLOWING | PRESS ONCE TO CLEAR LOG |
| ALCOHOL PRESENT PLEASE WAIT | PASS BAC = .000% | LOG CLEARED |
| ALCOHOL PRESENT PLEASE WAIT | ANALYSING SAMPLE BAC = .037% | PLEASE DOWNLOAD |
| | OVERLIMIT!!! BAC = .050% | |

FIG. 3

BREATH ANALYSIS DEVICE

This is a continuation of application Ser. No. 07/895,567, filed on Jun. 5, 1992, now abandoned, which is a continuation of Ser. No. 07/503,814, filed Apr. 3, 1990, now abandoned.

BACKGROUND OF THE INVENTION

The present invention relates to breath analysis devices, and in particular, to a breath analysis device which is capable of passive or direct sampling of an exhaled breath sample.

Police Departments conducting roadside screening of motorists in relation to breath analysis, are currently required by law to require mouthpiece sampling of the breath when requested by the police officers at a random breath testing station. This process involves the officer requesting that a sample of breath be given through a mouthpiece to an instrument, to which the police officer will take appropriate action according to the result. Currently all breath testing is conducted in this way and the Police Departments have a mammoth task in purchasing and distributing many thousands of mouthpieces each year.

One disadvantage with this is that a mouthpiece is used for each random breath test, and the cost of using such mouthpieces is unnecessary if the motorist has not been drinking or consumed any alcohol in the last few hours.

SUMMARY OF THE INVENTION

The object of the present invention is to provide a breath analysis device which obviates the need to use a mouthpiece on all random breath testing occasions.

According to one aspect of the present invention there is disclosed a dual breath analysis device having a passive first mode of testing and analysing an exhaled breath sample without use of a mouthpiece, and a direct second mode of testing and analysing a second breath sample through a mouthpiece apparatus.

The use of the dual breath analysis device of the present invention is to eliminate the need to use a mouthpiece for those motorists who have not taken a drink in recent hours whereas the remaining small percentage of motorists showing a positive alcohol presence during the passive testing mode will then go through a standard deliverance of a breath sample using a mouthpiece in the direct second mode.

BRIEF DESCRIPTION OF THE DRAWINGS

One embodiment of the present invention will now be described with reference to the drawings in which:

FIG. 3 is a display table illustrating the different displays of the device of the preferred embodiment.

DETAILED DESCRIPTION OF THE INVENTION

Figure 1:
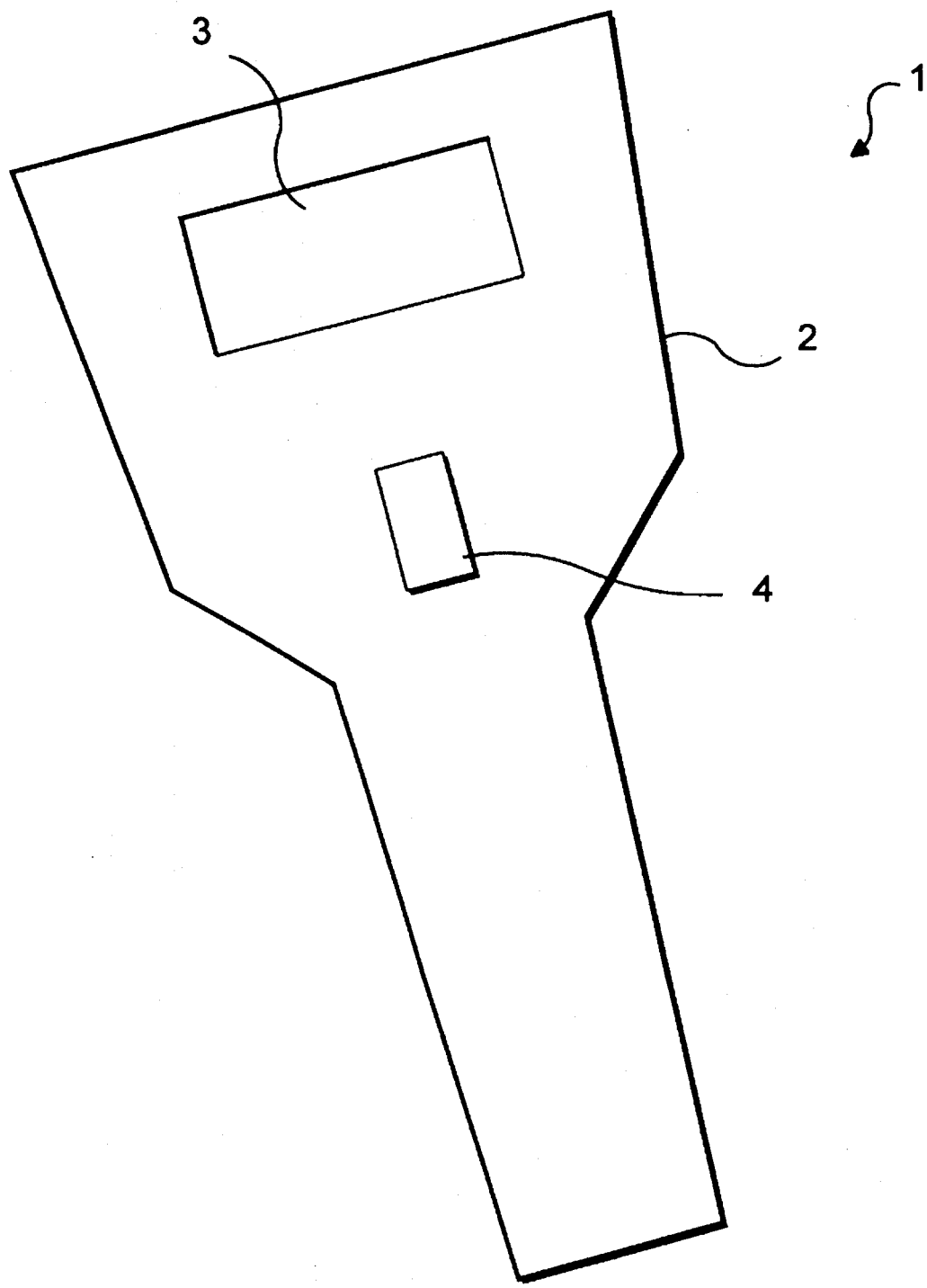
FIG. 1 is a perspective view of a hand held device of the preferred embodiment.
Figure 2:
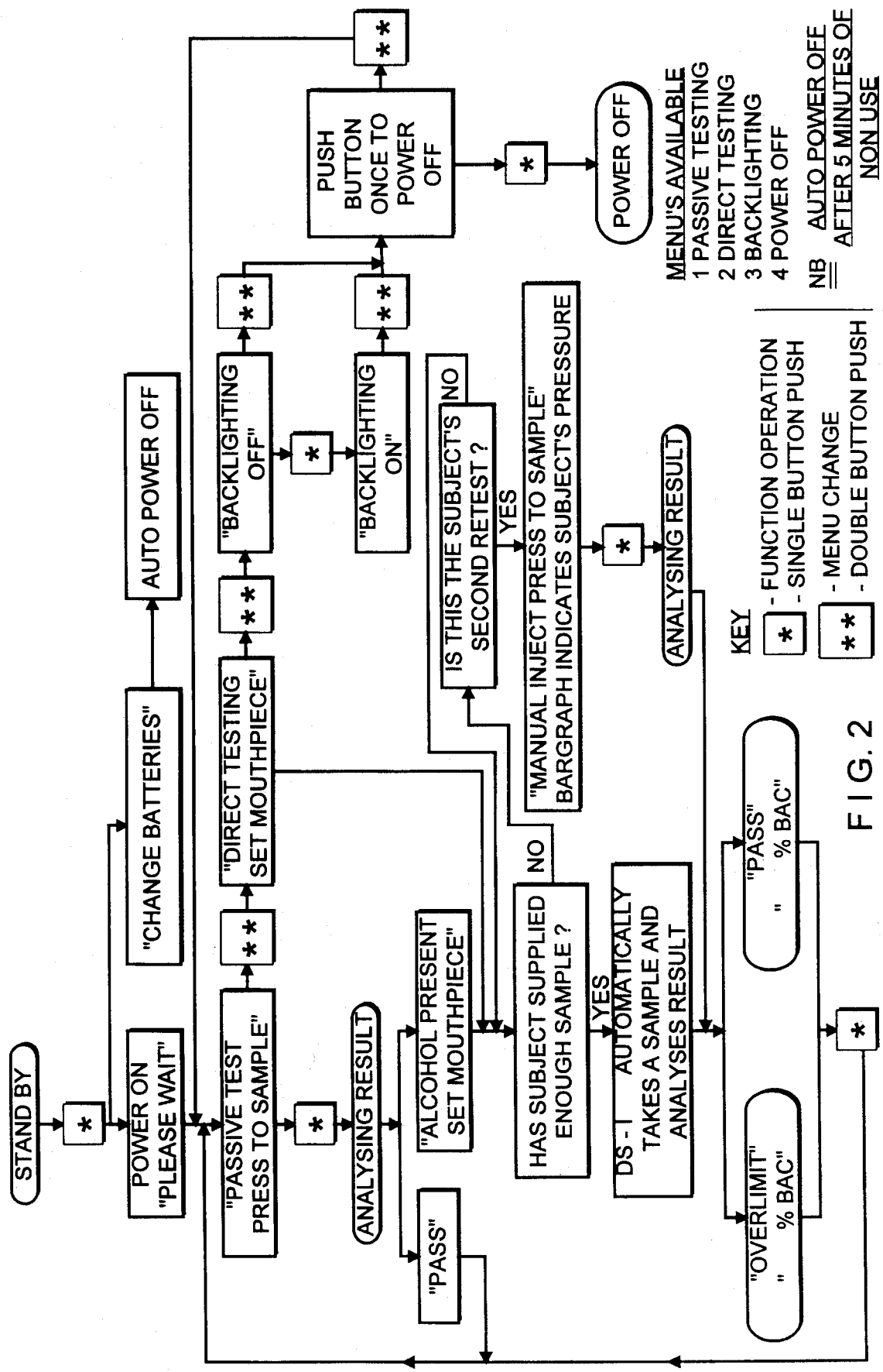
FIG. 2 is a flow diagram of the operation of the device of the preferred embodiment.

The device 1 illustrated in FIG. 1 comprises a hand held housing 2 having a display 3, a push button 4, a sensor (not shown), a sample port (not shown) and a fuel cell (not illustrated) for testing alcohol content of the sampled breath.

The device 1 uses four AA cells and has automatic power shut-off after five minutes of inactivity. The device is capable of conducting at least 800 passive and direct breath tests on one set of batteries. The display 3 which is an alpha-numeric LCD read out has backlighting for night time use. A microprocessor (not illustrated) automatically eliminates the read out at pre-programmed time.

The single push-button 4 is provided to select a number of operational modes through multiple actuation. The number of operational modes includes:

A. Passive Testing

B. Direct Testing with Low Volume Override

C. Battery/Testing Life

D. Diagnostic Check

E. Print Data

F. Auto Calibration

Mode D, E, and F are supervisory only and provide for mode alterations using an external module.

The microprocessor also records both modes of breath testing. The passive test is recorded as either a pass or fail and if a direct test was conducted after a fail was recorded, the direct test records specific details of date, time, breath alcohol content, and pass or fail.

The print data mode is used to download a stored information onto a printer via a RS232 port. Sufficient capacity is available for the results of two weeks of daily roadside testing.

The device is provided with a diagnostic check which provides for ease of servicing and setting up procedures for real time clock and checks of instruments operating parameters, exclusively only through the supervisory mode.

Another mode which requests a supervisory pass word in order to enter the mode of operation which concerns fine tuning of the instrument calibration is the automatic calibration mode. A known simulator solution is used and the instrument is calibrated by pressing the button to correct the span shown on the LCD. This mode provides a calibrator range of ±30% and shows a "Out of Service" command if a service is required.

Fuel Cell Response Analysis

The output voltage of a fuel cell of this type as a result of receiving a sample of oxidizable gas has been examined (Huck, 1969).

Examples of the response of a typical cell to individual samples of ethyl and methyl alcohols are well documented. The equation that has been proposed is:

$$v(t) = \frac{Vo}{\frac{k2}{k1} - 1} [\exp(-k1t) - \exp(-k2t)]$$

where k1=reation rate at the electrode (sec−1)

k2=discharge rate of the cell (sec−1)

Vo=maximum voltage achieved on open circuit

The determination of k1 and k2 by numerical analysis routines can be difficult and iterative procedures can prove to be unstable in functions of this form. However, we are not primarily interested in the amplitude and so if we apply the transformation $$z(t) = \frac{v(2t)}{v(t)}$$

we obtain $$Z(t) = \exp(-k_1 t) + \exp(-k_2)$$

This function poses a relatively simple task for analysis. Examining the function at three time values, t, 2t, 4t, yields z(t), z(2t) and hence $$k_1 = \frac{1}{t} \log \frac{[z(t) \pm 2z(2t) - z2(t)]}{2}$$

The response of several fuel cells to samples of ethyl alcohol and for other alcohols including methyl, butan-l-ol, propan-l-ol was examined. The error in the value of k1 obtained for these alcohols showed a trend suggesting a deviation from equation (4) to include higher orders of k1. This investigation will continue. However, values of z(t) with the range of alcohols studies showed excellent descrimination for values of t in a particular time range. This was the basis of a technique to show the presence of trace contaminants in a sample of ethyl alcohol.

The device also ensures a delivery of a prescribed amount of deep alveolar air using a pressure transducer volumetric measurement system which ensures that a person delivers a minimum of 1.3 liters of breath when the instrument is in the direct sampling mode, thus enhancing the overall accuracy of the instrument.

Figure 4:
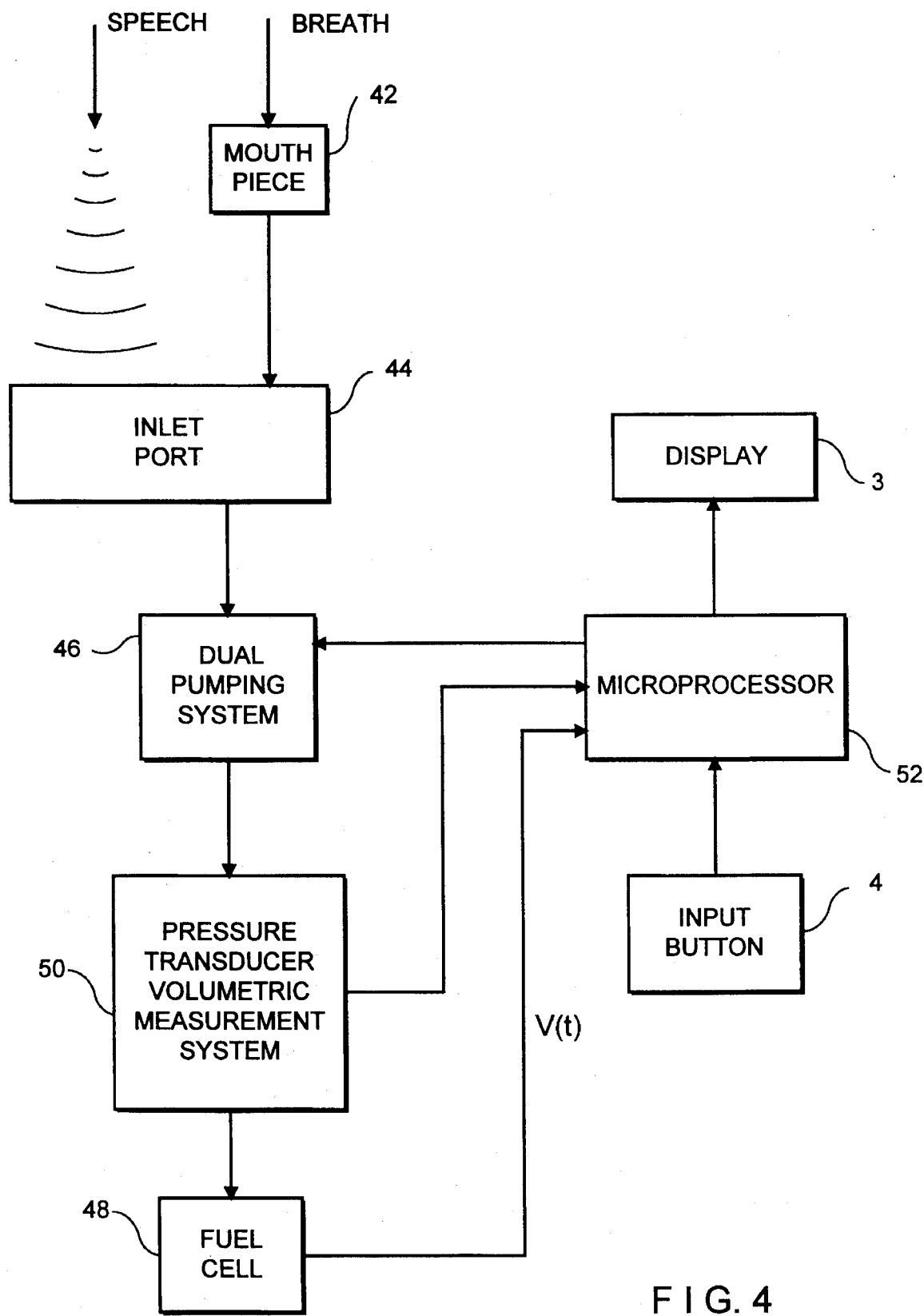
FIG. 4 illustrates the operating components of the system.

The microprocessor is incorporated to provide multiple functions which include:

a) Control of all modes
b) Actuate the dual pumping systems
c) Indicate the conditions of operation
d) Record data logging of daily testing
e) Provide user information and assistance FIG. 4 illustrates the operating components of the system. The microprocessor 52 is coupled to the fuel cell 48, the dual pumping system 46, and the pressure transducer volumetric measurement system 50. The mouthpiece 42 can be utilized with the inlet port 44 for obtaining the sample.

The foregoing describes only one embodiment of the present invention, and modifications obvious to those skilled in the art can be made thereto without departing from the scope of the present invention.

What we claim is:

1. A dual breath analysis device for testing and analysing an exhaled breath sample, said device comprising:

a housing;

a sample port coupled to said housing for receiving said exhaled breath sample and being connectable to a mouthpiece apparatus;

a fuel cell for generating a breath alcohol signal in response to said exhaled breath sample;

a dual pumping system coupled to said sample port for pumping said exhaled breath sample to said fuel cell in a passive test mode and for coupling said sample port to said fuel cell for a person to provide said exhaled breath sample at a positive pressure using said mouthpiece apparatus in a direct test mode;

a pressure transducer volumetric measurement system coupled between said sample port and said fuel cell for measuring said exhaled breath sample in said direct test mode;

control means coupled to said dual pumping system, said pressure transducer volumetric measurement system and said fuel cell, said control means for actuating said dual pumping system and for receiving a volumetric measurement from said pressure transducer volumetric measurement system and said breath alcohol signal from said fuel cell, said control means for performing a pass/fail test on a first breath alcohol signal obtained from a first breath sample without using said mouthpiece apparatus in said passive test mode;

in response to detecting the presence of alcohol in said first breath sample by performing said pass/fail test on said first blood alcohol signal, said control means accurately measuring BAC of a second breath alcohol signal obtained from a second breath sample comprising deep alveolar air obtained using said mouthpiece apparatus when said volumetric measurement exceeds a prescribed volume in said direct test mode.

2. A device according to claim 1 wherein said prescribed volume of deep alveolar air is a minimum of 1.3 liters.

3. A device according to claim 1 wherein said control means comprises a microprocessor.

4. A device according to claim 3 wherein said microprocessor provides the following functions:

a) control of all modes;
   b) indicate the conditions of operation;
   c) record data logging of daily testing; and
   d) provide user information.

* * * * *